United States Patent [19]

Tomidokoro et al.

[11] 4,248,801

[45] Feb. 3, 1981

[54] PROCESS FOR THE PRODUCTION OF TERTIARY AMINE HAVING LONG CHAIN ALKYL GROUP

[75] Inventors: Susumu Tomidokoro, Funabashi; Michito Sato, Yokohama; Daini Saika, Chiba, all of Japan

[73] Assignee: The Lion Fat & Oil Co., Ltd., Tokyo, Japan

[21] Appl. No.: 54,457

[22] Filed: Jul. 3, 1979

[30] Foreign Application Priority Data

Jul. 4, 1978 [JP] Japan ................... 53-81203

[51] Int. Cl.$^3$ ............... C07C 85/08; C07C 85/20; C07C 85/24
[52] U.S. Cl. .................. 564/463; 564/489; 564/490
[58] Field of Search ........... 260/583 R, 583 H, 583 K

[56] References Cited

U.S. PATENT DOCUMENTS

| | | | |
|---|---|---|---|
| 2,355,356 | 8/1944 | Young | 260/583 K |
| 3,136,819 | 6/1964 | Shapiro et al. | 260/583 R |
| 4,003,933 | 1/1977 | Drake | 260/583 K |

FOREIGN PATENT DOCUMENTS 759291 10/1956 United Kingdom ............... 260/583 H Primary Examiner—John Doll
Attorney, Agent, or Firm—Armstrong, Nikaido, Marmelstein & Kubovcik

[57] ABSTRACT

Tertiary monomethylamines having long chain alkyl groups are advantageously prepared from unsaturated aliphatic nitriles under a low pressure at a high yield by the steps of:
(a) reducing the nitriles with hydrogen in the presence of a nickel hydrogenation catalyst at 200° through 230° C. and under a hydrogen pressure of 0 through 10 kg/cm$^2$G, while the formed ammonia is removed;
(b) reacting the resultant amines with a hydroxymethylation agent in the presence of the nickel catalyst at 150° through 180° C., while hydrogen is passed through the reaction zone under 0.3 through 7 kg/cm$^2$G and the formed water is removed, and;
(c) reducing the resultant tertiary amines with hydrogen in the presence of the nickel catalyst at 175° through 210° C. and under a hydrogen pressure of 5 through 10 kg/cm$^2$G.

7 Claims, No Drawings

PROCESS FOR THE PRODUCTION OF TERTIARY AMINE HAVING LONG CHAIN ALKYL GROUP

This invention relates to a process for producing tertiary amines, and more particularly, it relates to a process for producing tertiary monomethylamines having long chain alkyl groups by using, as a starting material, unsaturated aliphatic nitriles under a low reaction pressure at a good yield.

Long chain aliphatic amines are produced by using, as a starting material, nitriles which are mainly derived from natural fats and oils. The starting nitriles are mixtures of unsaturated nitriles and saturated nitriles. Accordingly, in the case where long chain dialkyl monomethylamines are produced which are a starting material for products such as surface active agents, the hydrogenation of the unsaturated bonds, the hydrogenation of the nitrile group or groups and the methylation of the formed amino group or groups should be effected.

Conventional processes for producing such saturated amines generally comprise the steps of simultaneous reduction of the unsaturated bonds and the nitrile groups, of long chain aliphatic nitriles having an unsaturated bond or bonds with hydrogen under a high temperature and a high pressure, to thereby form secondary long chain alkyl amines and, then, N-methylation of the resultant amines to form tertiary long chain dialkyl monomethylamines. For example, U.S. Pat. No. 2,355,356 and British Pat. No. 759,291 disclose the preparation of long chain aliphatic secondary amines from nitriles. In addition. U.S. Pat. No. 3,136,819 and British Pat. No. 1403569 disclose the preparation of tertiary amines by the N-methylation of primary or secondary amines.

However, these conventional processes involve the problems that, since a high pressure is required for the hydrogenation, the reduction apparatus is expensive, and the operation and maintenance of the apparatus are difficult. If the hydrogenation is carried out under a lowered pressure in order to avoid the above-mentioned high pressure problems, a long period of reaction time is required and the generation of undesirable by-products, tertiary long chain alkyl amines become remarkable.

Accordingly, the objects of this invention are to obviate the above-mentioned problems in the conventional long chain aliphatic amine production processes and to provide an improved process for producing a desired tertiary long chain dialkyl monomethylamine under a low pressure.

The other objects of this invention are to effect said reaction smoothly and to prevent the production of undesired tertiary long chain alkyl amines as by-products in said reaction.

In accordance with this invention, there is provided a process for preparing tertiary monomethylamines having long chain alkyl groups comprising the steps of:

(a) reducing at least one unsaturated aliphatic nitrile having from 8 to 24 carbon atoms, or a mixture of nitriles containing at least one unsaturated aliphatic nitrile having from 8 to 24 carbon atoms with hydrogen, in the presence of a nickel hydrogenation catalyst, under the conditions of a reaction temperature of from 200° to 230° C. and a hydrogen pressure of from 0 to 10 kg/cm$^2$G, while the formed ammonia is removed, to thereby form a mixture of amines mainly containing secondary long chain aliphatic amines (an amination step);

(b) reacting the resultant mixture of amines with a hydroxymethylation agent in the presence of a nickel hydrogenation catalyst, at a reaction temperature of from 150° to 180° C., while hydrogen is passed through the reaction zone under a hydrogen pressure of from 0.3 to 7 kg/cm$^2$G and the formed water is continuously removed from the reaction zone, to thereby form a mixture of tertiary amines mainly containing tertiary long chain aliphatic monomethylamines (a methylation step), and;

(c) reducing the resultant mixture of tertiary amines with hydrogen in the presence of a nickel hydrogenation catalyst, under the conditions of a reaction temperature of from 175° to 210° C. and a hydrogen pressure of from 5 to 10 kg/cm$^2$G, to thereby effect the hydrogenation of the unsaturated bonds of the tertiary amines (a reduction step).

Thus, it has been found that the above mentioned objects of this invention can be achieved by the combination of: (i) the hydrogenation of the unsaturated bonds of the starting nitriles and the hydrogenation of the nitrile groups of the starting nitriles being separately carried out (both reactions are simultaneously carried out in the conventional processes); (ii) the hydrogenation of the unsaturated bonds being carried out in the last step, and; (iii) the methylation step being carried out between the amination step and the reduction step.

The starting materials used in the production process according to this invention include unsaturated aliphatic nitriles having from 8 to 24 carbon atoms, any mixture thereof and a mixture thereof with saturated nitriles. These starting materials can be derived from various natural fats and oils. Examples of such unsaturated aliphatic nitriles are oleonitrile, tallow nitriles, soya nitriles, palm nitriles, rape nitriles, coco nitriles and others.

The hydrogenation catalysts used in each step of this invention include nickel hydrogenation catalysts having a high activity in order to effect a smooth reaction and to depress the production of undesired by-products. Especially, nickel hydrogenation catalysts supported on a carrier, for example, nickel catalysts supported on an inert carrier such as diatomaceous earth, alumina, silica-alumina and the like, can be effectively used in this invention. In addition, a Raney nickel catalyst can also be used. The catalyst which has been used in the first step can be directly used, as a catalyst, in the subsequent methylation step and hydrogenation step of the unsaturated bond as it is. These nickel hydrogenation catalysts can be used alone or any combination thereof.

Each of the three steps of this invention now will be explained in detail.

A: Amination step

This amination step is carried out by reducing said unsaturated aliphatic nitriles or a mixture containing the same with hydrogen in the presence of a nickel hydrogenation catalyst under the conditions of a reaction temperature of from about 200° to about 230° C. and a hydrogen pressure of from 0 to about 10 kg/cm$^2$G (gauge pressure), while the formed ammonia is distilled off. The hydrogen is continuously fed to the reaction system and is removed from the system together with the formed ammonia.

Although there is no critical limitation, the suitable amount of the hydrogenation catalyst to be used in this step is within the range of from about 0.1 to about 0.5 parts by weight, based on 100 parts by weight of the starting nitriles.

In the practice of this step, the starting nitriles and the catalyst are first charged to a reactor and, then, hydrogen is passed through the reactor with stirring. The hydrogen pressure is maintained within the range of from about 0 to about 10 kg/cm$^2$G (gauge pressure) and, more preferably, from about 0 to about 6 kg/cm$^2$G. When the hydrogen pressure is more than about 10 kg/cm$^2$G, since the solubility of ammonia in the system increases due to the high pressure of the system, the conversion of the primary amines to the secondary amines is depressed, and, therefore, the reaction time for obtaining a desirable high yield of the secondary amines becomes long and also the amount of the undesirable by-products, the long chain aliphatic tertiary amines, increases. Contrary to this, when the hydrogen pressure is less than about 0 kg/cm$^2$G, since the reaction is carried out under a reduced pressure, the reaction procedure is troublesome and the reaction rate remarkably decreases.

In this step, in order to obtain the desired secondary amines at a high selectivity and at a nitrile conversion of approximately 100% in a one stage reaction, it is required that the reaction temperature be within a narrow limited range, that is, within the range of from about 200° to about 230° C., and that the ammonia formed during the course of the reaction be removed out of the reaction system. Especially, the reaction should be carried out in such a manner that 85% by weight or more of the ammonia, based on a theoretical amount of the ammonia to be formed, is removed from the system for a reaction period of two hours or less. When the reaction temperature is not more than about 220° C., the formation ratio of the tertiary amines is small. However, when the reaction temperature is more than about 230° C., a rapid increase in the amount of the formed tertiary amines unpreferably occurs. Since the hydrogenation of the nitriles is exothermic, the reaction temperature tends to exceed about 230° C. In such cases, the reaction temperature should be maintained within the above-mentioned range by an external cooling. On the other hand, the reaction should be carried out at about 200° C. or more. When the reaction temperature is less than about 200° C., the reaction rate becomes slow and, therefore, a long reaction period is required. As a result, the production amount of the undesired tertiary amines unpreferably increases. However, it should be noted that, when the reaction mixture is heated to a given reaction temperature, supply of hydrogen in the reactor from a temperature of less than 200° C., for example, approximately 150° C., is not excluded for activating the catalyst and avoiding a violent reduction reaction. Thus, in this step, the reduction reaction should substantially occur at a temperature not exceeding about 230° C. and not less than about 200° C.

When the secondary amines are prepared, the most important requirement for obtaining the secondary amines at a high selectivity is that the reaction is carried out in such a manner that 85% by weight or more of the ammonia, based on a theoretical amount of the ammonia to be formed, is removed from the system for a reaction period of two hours or less. The theoretical amount of the ammonia to be formed means the amount of the ammonia to be formed in the case where the starting nitriles are entirely converted to the secondary amines. The reaction period is the reaction time from the point when the temperature of the contents in the reactor reaches 200° C. That is to say, in accordance with this invention, the reaction is carried out in such a manner that the rate of the initial reaction is as high as possible and the formed ammonia is rapidly removed from the system. For this purpose, the uses of the above-mentioned catalyst having a high activity and the above-mentioned limited reaction temperature range are essential for this invention, and the flow rate of the hydrogen which passes through the reaction system and the hydrogen pressure should be appropriately determined. The ammonia can be easily removed and the production of the by-product, i.e. the tertiary amines can be depressed, as the hydrogen pressure decreases.

As mentioned above, the hydrogenation of the aliphatic nitriles under the special conditions generally completes the reaction in a short time of period, e.g. 3 through 6 hours, and produces the desired secondary amines at a yield of 90% or more.

B: Methylation step

In this step, the mixture of the amines obtained in the above described first step is reacted with a hydroxymethylation agent in the presence of the nickel hydrogenation catalyst, under the conditions of a reaction temperature of about 150° to about 180° C. and a hydrogen pressure of about 0.3 to about 7 kg/cm$^2$G, while hydrogen passes through the system and the water formed in the reaction is removed from the system. Since the nickel hydrogenation catalyst used in the first step can be used, as it is, in this step, no addition of the catalyst is usually required. In addition, since the reaction temperature of the first step is high, the treatment for activating the catalyst is not necessary in this step. In the case where a fresh catalyst is used in this step, the catalyst is treated with hydrogen for 30 minutes or more, under the conditions of a temperature of 180° through 230° C. and a hydrogen pressure of 0.5 through 10 kg/cm$^2$G. When the reaction is carried out batchwise, the activation of the catalyst can be effected in the starting amines.

The hydroxymethylation agent for the secondary amines used in this invention is preferably formaldehyde. The formaldehyde can also be utilized as formaldehyde polymers, such as trioxane, paraformaldehyde and the like. The formaldehyde is conveniently utilized in the form of formalin. The amount of the formaldehyde used in this invention is 1.0 equivalent or more, and preferably, 1.05 through 1.5 equivalent, based on 1.0 equivalent of the starting amines.

In order to smoothly effect the hydroxymethylation and hydrogenation of the secondary amines in the presence of hydrogen, and to prevent the reaction of the starting secondary amines with primary amines contained in the secondary amines as impurities, and the production of undesired by-products, that is, tertiary amines having three long chain aliphatic (e.g. alkyl and alkenyl) groups, the reaction should be carried out under the reaction conditions of a reaction temperature of about 150° through about 180° C. and a hydrogen pressure of about 0.3 through about 7 kg/cm$^2$G, in such a manner that the hydrogen is fed so as to pass through the reaction system and is continuously removed out of the system together with the steam formed in the reaction. When the hydrogen pressure in the reaction system is out of the range of about 0.3 through about 7 kg/cm$^2$G, the yield of the methylation product obtained in this step unpreferably decreases. The preferable hydrogen pressure is within the range of from 0.5 through 5 kg/cm$^2$G. The reaction rate is maximized under a hydrogen pressure of 1 through 4 kg/cm$^2$G. When the reaction temperature exceeds 180° C., the production of the undesired by-products i.e., tertiary long chain aliphatic amines becomes remarkable. On the other hand, since the rate of N-methylation reaction decreases as the reaction temperature decreases, the reaction temperature is preferably 150° C. or more.

C: Reduction step

In this step, the tertiary long chain alkyl monomethylamines prepared in the above described second step are reduced with hydrogen in the presence of the nickel hydrogenation catalyst, under conditions of a reaction temperature of from about 175° to about 210° C. and a hydrogen pressure of from about 5 to about 10 kg/cm$^2$G.

When the reaction temperature of this step is more than about 210° C., since a demethylation reaction of the tertiary long chain aliphatic monomethylamines occurs together with the reduction reaction of the unsaturated bonds, the content of the tertiary dialkyl methylamines in the product unpreferably decreases. Contrary to this, when the reaction temperature is less than 175° C., the hydrogenation of the unsaturated bonds does not satisfactorily occur. The best result is obtained at a temperature of 180° through 200° C. In addition the result of the hydrogenation becomes better as the reaction pressure (i.e. hydrogen pressure) increases. However, since the only substantially same results are obtained, when the reaction pressure is more than 8 kg/cm$^2$G, an extra high pressure is not preferable from an economical point of view. For this reason, the reaction pressure of the third step is suitably within the range of from about 5 to about 10 kg/cm$^2$G, and preferably, within the range of from 7 to 10 kg/cm$^2$G.

The above-mentioned amination step, methylation step and reduction step should be carried out in that order. If the amination and the reduction are simultaneously carried out in the first step, the amount of the tertiary trialkylamines in the products unpreferably increases. This is because, when the tertiary dialkyl methylamines are produced from long chain aliphatic nitriles having an unsaturated double bond or bonds under a low reaction pressure of 10 kg/cm$^2$G or less, a long reaction period is required for obtaining the secondary dialkylamines in the first step. The long reaction period causes an increase in the production amount of the tertiary trialkylamines, which adversely effect the quality of the amine products.

If the reduction step is carried out after the amination step but before the methylation step, the amount of the undesired trialkylamines unpreferably increases unless the reduction reaction is effected under a high pressure. When the reduction step is carried out under a lowered pressure, a long reaction period is required for reducing the unsaturated amines. Then, the long reaction period causes an increase in the production amount of the undesired trialkylamines. Thus, in order to produce tertiary long chain alkyl monomethylamines from unsaturated long chain aliphatic nitriles under a lowered pressure, the combination of the amination, methylation and reduction steps, in that order, is essential according to this invention.

This invention will now be further illustrated by, but is by no means limited to, the following Examples, in which all percentages are expressed on a weight basis unless otherwise noted.

EXAMPLE 1

Into a 1 liter autoclave equipped with an agitator, 500 g of tallow fatty nitriles and 1 g of nickel-diatomaceous earth catalyst were charged. Hydrogen was passed through the autoclave with stirring, while the hydrogen pressure was maintained at 5 kg/cm$^2$G and the contents of the autoclave was heated. After the temperature reached 220° C., the hydrogen continued to flow through the autoclave at 220° C., for 2.5 hours, while the hydrogen pressure was maintained at 5 kg/cm$^2$G. Ammonia was generated as the reaction occurred. The gaseous ammonia which flowed out of the autoclave together with the hydrogen was absorbed into 50% sulfuric acid. The flow rate of the outlet gas from the autoclave was measured after the absorption of the gaseous ammonia, and this flow rate was adjusted to 0.35 liter (20° C. at atmospheric pressure) per minute, based on 1 mol of the nitrile. Approximately 93% of the ammonia, based on the theoretical amount of the ammonia formed in the reaction (i.e. the production amount of the ammonia formed in the reaction in the case, where the nitriles were entirely converted to the secondary amines), was removed from the reaction system for 2 hours after the reaction temperature reached 200° C.

After the reaction mixture was agitated for 2.5 hours at 220° C., the temperature was reduced to 170° C. Then, 89 g of formalin containing 37% formaldehyde were continuously and dropwise added over 2.5 hours, with stirring, at a temperature of 170° C. and under a hydrogen pressure of 3 kg/cm$^2$G, while the hydrogen was passed through the autoclave. The flow rate of the outlet gas from the autoclave was adjusted to 0.4 liter (20° C. at atmospheric pressure) per 1 mol of the amines. After the formalin was added, the hydrogen flow was stopped and the reaction mixture was stirred for a further 3 hours, at a temperature of 200° C. and under a hydrogen pressure of 9 kg/cm$^2$G.

After the reaction, the reaction temperature was reduced to 70° C. and the catalyst was removed from the reaction mixture by filtration. Thus, 496 g of the amine product containing 97.3% of the tertiary amines was obtained.

The tertiary amines in the amine product, contained 3.9% of the alkyl dimethylamines, 92.0% of the dialkyl methylamines and 3.6% of the trialkylamines. The iodine number of this amine product was 3.2, which showed that substantially all of the unsaturated bond or bonds of the aliphatic groups of the amines were saturated.

Comparative Example 1

After tallow fatty nitriles were converted to the amines in a manner as described in the first step of Example 1, the amines thus obtained were hydrogenated in a manner similar to that described in the third step of Example 1 and, then, an N-methylation reaction was carried out in a manner similar to that described in the second step of Example 1. After the completion of the reaction, the catalyst was removed from the reaction mixture in the manner described in Example 1. Thus, 495 g of the amines having an iodine number of 3.5 and containing 98.2% of the tertiary amines were obtained. However, said tertiary amines contained 2.7% of the monoalkyl dimethylamines, 89.8% of the dialkyl methylamines and 7.0% of the trialkylamines. As is clear from the above results, since the reduction step was carried out prior to the N-methylation step in this Comparative Example 1, the amount of the produced dialkyl monomethylamines was decreased and the amount of the produced undesired trialkylamines increased compared to Example 1.

Comparative Example 2

After tallow fatty nitriles were converted to the corresponding amines in a manner described in the first step of Example 1, the reaction was further continued until the iodine number of the product was 4 or less. Thus, after 6.5 hours reaction in total, the iodine number of the product was 3.7. Then, an N-methylation reaction of the product was carried out in a manner described in the second step of Example 1.

After the methylation reaction, the catalyst was removed from the reaction mixture in a manner described in Example 1. Thus, the amine product containing 98.0% of the tertiary amines was obtained. However, this tertiary amines contained 2.0% of the alkyl dimethylamines, 90.0% of the dialkyl methylamines and 7.5% of the trialkylamines.

Comparative Example 3

Tallow fatty nitriles were converted to the corresponding amines in a manner described in the first step of Example 1 and, then, the amines thus obtained were subjected to an N-methylation reaction in a manner described in the second step of Example 1. Thereafter, the hydrogenation reaction of the third step of Example 1 was repeated, except that the reaction temperature was 240° C.

After the completion of the reaction, the catalyst was removed in a manner described in Example 1. Thus, the amine product containing 78.3% of the tertiary amines was obtained.

EXAMPLE 2

Tallow fatty nitriles were subjected to the amination reaction and the subsequent N-methylation reaction in the manners described in the first and second steps of Example 1. Then, the reaction mixture thus obtained was hydrogenated at a temperature of 200° C. and under a hydrogen pressure of 8 kg/cm$^2$G in a manner described in the third step of Example 1.

After the completion of the reaction, the catalyst was removed from the reaction mixture in a manner described in Example 1 and 492 g of the amine product containing 98.2% of the tertiary amines was obtained. The tertiary amines contained 4.1% of the alkyl dimethylamines, 91.9% of the dialkyl methylamines and 3.5% of the trialkylamines, and the iodine number of the product was 3.5.

EXAMPLE 3

Into a 1 liter autoclave, 500 g of tallow fatty nitriles and 1 g of nickel-diatomaceous earth catalyst were charged. An amination reaction was carried out at a temperature of 220° C. and a hydrogen pressure of 9 kg/cm$^2$G, for 3 hours, in a manner described in the first step of Example 1. 91% of the gaseous ammonia based on the theoretical amount was discharged from the autoclave for about 2 hours after the reaction temperature reached 200° C. Thereafter, an N-methylation reaction was carried out in a manner described in the second step of Example 1 and, then, the hydrogenation reaction described in the third step of Example 1 was carried out for 1.5 hours.

After the completion of the reaction, the catalyst was removed in a manner similar to that described in Example 1. Thus, an amine product containing 97.8% of the tertiary amines and having an iodine number of 2.8 was obtained. The tertiary amines contained 4.1% of the alkyl dimethylamines, 91.0% of the dialkyl methylamines and 4.5% of the trialkylamines.

EXAMPLE 4

Into a 1 liter autoclave, 500 g of distilled tallow fatty nitriles and 1 g of nickel-alumina catalyst were charged. An amination reaction was carried out at a temperature of 220° C. and under a hydrogen pressure of 0.5 kg/cm$^2$G, for 4 hours, in a manner described in the first step of Example 1. 86% of the ammonia, based on the theoretical amount, was discharged from the autoclave for about 2 hours after the reaction temperature reached 200° C. Thereafter, an N-methylation reaction was carried out in a manner described in the second step of Example 1 and, then, a hydrogenation reaction was carried out at a temperature of 200° C. and a hydrogen pressure of 9 kg/cm$^2$G, for 2 hours, in a manner described in the third step of Example 1.

After the completion of the reaction, the catalyst was removed in a manner described in Example 1. Thus, an amine product containing 97.3% of the tertiary amines and having an iodine number of 2.6 was obtained. This tertiary amines contained 3.7% of the alkyl dimethylamines, 93.6% of the dialkyl methylamines and 2.7% of the trialkylamines.

What we claim is:

1. A process for preparing tertiary monomethylamines having long chain alkyl groups comprising the following sequence of (a) amination, (b) methylation and (c) reduction steps:
    (a) reducing at least one unsaturated aliphatic nitrile having from 8 to 24 carbon atoms, or a mixture of nitriles containing at least one unsaturated aliphatic nitrile having from 8 to 24 carbon atoms with hydrogen, in the presence of a nickel hydrogenation catalyst, under the conditions of a reaction temperature of from 200° to 230° C. and a hydrogen pressure of from 0 to 10 kg/cm$^2$G, while the formed ammonia is removed in a manner such that at least 85% by weight of the ammonia, based on the theoretical amount, is removed from the reaction system in a reaction time of two hours or less, to thereby form a mixture of amines mainly containing secondary long chain aliphatic amines;
    (b) reacting the resultant mixture of amines with a hydroxymethylation agent in the presence of a nickel hydrogenation catalyst at a reaction temperature of from 150° to 180° C., while hydrogen is passed through the reaction zone under a hydrogen pressure of from 0.5 to 5 kg/cm$^2$ G and water is continuously removed from the reaction zone, to thereby form a mixture of tertiary amines mainly containing tertiary long chain aliphatic monomethylamines; and
    (c) reducing the resultant mixture of tertiary amines with hydrogen in the presence of a nickel hydrogenation catalyst, under the conditions of a reaction temperature of from 175° to 210° C. and a hydrogen pressure of from 5 to 10 kg/cm$^2$G, to thereby effect the hydrogenation of the unsaturated bonds of the tertiary amines.

2. A process as claimed in claim 1, wherein said nickel hydrogenation catalyst is selected from Raney nickel and nickel catalysts supported on diatomaceous earth, alumina and silica-alumina.

3. A process as claimed in claim 1, wherein said hydroxymethylation agent is selected from formaldehyde, formaldehyde polymers and any mixtures thereof.

4. A process as claimed in claim 1, wherein said hydrogen pressure in the amination step (a) is within the range of from 0 to 6 kg/cm$^2$G.

5. A process as claimed in claim 1, wherein said hydrogen pressure in the methylation step (b) is within the range of from 1 to 4 kg/cm$^2$G.

6. A process is claimed in claim 1, wherein said hydrogen pressure in the reduction step (c) is within the range of from 7 to 10 kg/cm$^2$G.

7. A process as claimed in claim 1, wherein the amount of said nickel hydrogenation catalyst is within the range of from 0.1 to 0.5 parts by weight, based on 100 parts by weight of the starting nitriles.

* * * * *